United States Patent [19]

Muirhead et al.

[11] Patent Number: 4,742,051
[45] Date of Patent: May 3, 1988

[54] ANTIHYPERTENSIVE COMPOUNDS

[75] Inventors: Ernest E. Muirhead, Memphis; Byron E. Leach, deceased, late of Memphis, by Ellanor L. L. Leach, executor; Lawrence W. Byers, Memphis, all of Tenn.

[73] Assignee: University of Tennessee Research Corporation, Knoxville, Tenn.

[21] Appl. No.: 284,521

[22] Filed: Jul. 17, 1981

Related U.S. Application Data

[63] Continuation of Ser. No. 80,523, Oct. 1, 1979, abandoned, which is a continuation-in-part of Ser. No. 931,859, Aug. 7, 1978, Pat. No. 4,206,201, which is a continuation of Ser. No. 811,891, Jun. 30, 1977, abandoned.

[51] Int. Cl.⁴ .................. A61K 31/66; C07F 9/09
[52] U.S. Cl. ......................... 514/114; 260/403; 424/103; 514/76; 514/77; 558/169
[58] Field of Search ............... 260/403, 925, 944, 945; 424/199, 211, 103; 514/76, 77, 114; 558/169

[56] References Cited

U.S. PATENT DOCUMENTS

| Re. 28,903 | 7/1976 | Aneja et al. | 260/403 |
|---|---|---|---|
| 2,447,715 | 8/1948 | Rose | 260/403 X |
| 2,864,848 | 12/1958 | McArthur | 260/945 X |
| 3,282,788 | 11/1966 | Daniels et al. | 424/103 |
| 3,577,446 | 5/1971 | Rakhit | 260/403 |
| 3,683,070 | 8/1972 | Thuillier | 424/103 |
| 4,329,302 | 5/1982 | Hanahan et al. | 260/925 |

OTHER PUBLICATIONS

Muirhead et al., J. Lab. Clin. Med., vol. 67, (1966), pp. 778-791.
Muirhead et al., Clin. Sci. and Mol. Med., vol. 51, (1976), pp. 287s-290s.
Muirhead et al., Supp. to Annals Acad. Med., vol. 5, (1966), pp. 36-44.
Muirhead et al., Lab. Invest., vol. 35, (1977), pp. 162-172.
Muirhead, Contr. Nephrol., vol. 12, (1978), pp. 69-81.
Muirhead et al., "Antihypertensive Function of Renal Medulla", in Hypertensive Mechanisms and Management, Onest et al., editors, Greene & Stratton, Inc., (1973), pp. 631-643.
Muirhead et al., Chemical Abstracts, vol. 68, (1968), 37970w.
Muirhead et al., Chemical Abstracts, vol. 76, (1972), 81365s.
Muirhead et al., J. Lab. Clin. Med., vol. 56, (1960), pp. 167-180.
Muirhead et al., Arch. Path., vol. 80, (1965), pp. 43-49.

*Primary Examiner*—Richard Raymond
*Attorney, Agent, or Firm*—George W. Neuner

[57] ABSTRACT

Compounds are described having the formula

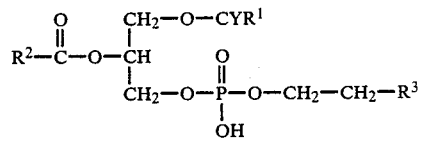

wherein
$R^1$ is an alkyl or alkenyl group having from about 11 to about 23 carbon atoms;
$R^2$ is hydrogen or an alkyl or alkenyl group having from about 1 to about 11 carbon atoms;
$R^3$ is $NR_4R_5$ or $NR_4R_5R_6^+An^-$
wherein $R_4$, $R_5$ and $R_6$ are independently hydrogen or lower alkyl having from 1 to 3 carbon atoms and An is an anion; and
Y represents the hydrogens of a methylene group or the oxygen of a carbonyl group.

These compounds are useful as vasodilators and antihypertensive agents.

23 Claims, No Drawings

ANTIHYPERTENSIVE COMPOUNDS

The invention described herein was made in the course of work under a grant or award from the United States Department of Health, Education and Welfare.

This application is a continuation of the application Ser. No. 80,523 filed Oct. 1, 1979 (now abandoned), which is a continuation-in-part of application Ser. No. 931,859 filed Aug. 7, 1978 (now U.S. Pat. No. 4,206,201), which in turn is a continuation of application Ser. No. 811,891 filed June 30, 1977 (now abandoned).

FIELD OF THE INVENTION

This invention is related to antihypertensive renomedullary lipids (ARL) and particularly to compounds that exhibit acute vasodilator as well as antihypertensive properties.

BRIEF BACKGROUND OF THE INVENTION

This invention is directed to an ARL compound that exhibits acute vasodilator as well as antihypertensive properties and to a class of compounds structurally related to the ARL compund that are acute vasodilator as well as antihypertensive properties and/or can be used as intermediates to produce such compounds. In the prior art, compositions were extracted from rabbit medulla and have been shown at high doses to provide antihypertensive activity and vasodepression activity (see Muirhead, E. E. et al., J. Lab. & Clin. Med. 56:167, 1960 and the other Muirhead et al. references in Proceedings of the Seminar on Hypertension, Supplement to Annals of Academy at Medicine, The Academy of Singapore, V.5, No. 3, July 1976, pp 36–44).

However, such prior compounds have been nonpolar, low in potency and in many cases the results were not reproducible, i.e., activity seemed to disappear on a batch by batch basis.

SUMMARY OF THE INVENTION

The present invention provides compounds of the formula:

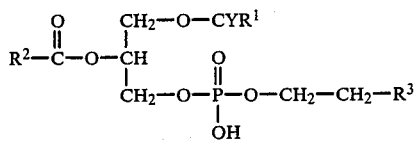

wherein $R^1$ is an alkyl or alkenyl group having from about 11 to about 23 carbon atoms;

$R^2$ is hydrogen or an alkyl or alkenyl group having from about 1 to about 11 carbon atoms;

$R^3$ is $NR_4R_5$ or $NR_4R_5R_6{}^+An^-$ wherein $R_4$, $R_5$ and $R_6$ are independently hydrogen or lower alkyl having from 1 to 3 carbon atoms and An is an anion; and Y represents the hydrogens of a methylene group or the oxygen of a carbonyl group. These compounds exhibit acute vasodilator as well as antihypertensive properties and are useful as intermediates for producing compounds that exhibit such properties.

Preferably vasodilator and antihypertensive agents of the present invention have the above formula wherein Y represents the two hydrogen atoms of methylene group, i.e. the substituent on the α-carbon is an ether.

These ether compounds provide substantially increased biological potency.

The compounds of the present invention exhibit a biological depressor effect activity of at least 0.2 units, preferably at least 10 units, and more preferably at least 40 units.

As used herein a "unit" of biological depressor effect activity is defined as the activity measured by determining the triangular area under a continuous graph of blood pressure of an approximately 380 gm rat injected intravenously with nitroprusside, one leg of the triangle being defined by the initial drop upon injection and the hypotenuse of the triangle being defined by the line depicting the gradual rise in pressure after the inital drop, wherein "one unit" of activity equals the area of the triangle per microgram of nitroprusside.

The activity of any compound in "units" can be determined by intravenously injecting a rat with a known amount of the compound, finding the area per microgram of compound and dividing by the standard for nitroprusside. The area of the triangle is conveniently found by measuring the initial vertical drop in pressure on the graph in millimeters and the horizontal distance in millimeters from the vertical drop to the sloped curve (hypotenuse) at the midpoint of the vertical drop and then multiplying the two.

By administering compounds of the present invention, it has now been possible consistently to reproduce antihypertensive activity and for the first time produce acute vasodilator activity, i.e., a reduction in blood pressure of 30–50% in less than one minute with extremely small doses, e.g., with a single dose of 5 to $20 \times 10^{-6}$ grams per kg of body weight (I.V.) of the isolated ARL compound as produced herein when administered to a rat. In addition, with this invention lowering of blood pressure is accomplished for periods of from 2 to 4 days in duration with four doses of $10-25 \times 10^{-6}$ grams of the ARL compound administered (I.V.) to the rat for two successive days.

Thus, the ARL compound of this invention is useful in mammals as vasodilators in conditions where afterload on the heart should be decreased (as an after load reducer), especially heart failure due to intrinsic disease of the heart muscle, e.g., cardiomyopathy, without producing substantial tachycardia (a side effect encountered with many acute vasodilators) or other dysfunction of the heart. The ARL compound of this invention would also be useful in treating cardiogenic shock, mitral regurgitation, acute myocardial infarction and protracted congestive heart failure at the doses above.

The ARL compound of this invention is also useful in mammals to treat high blood pressure (hypertension) by lowering arterial pressure. The ARL compound of the invention when used as antihypertensives would be administered a few times a day initially and then reduced maintenance doses would be administered to the mammal.

DESCRIPTION OF THE INVENTION

The compounds of this invention having the above formula are 1-0-alkyl-2-acyl-glycero-3-phosphoethylamines and 1-acyl-2-acyl-glycero-3-phosphoethylamines, the N-alkyl substituted derivatives thereof, and pharmaceutically acceptable salts thereof. These compounds can also be conveniently named as esters of phosphoric acid. These compounds can be entirely synthesized by routine chemical and biochemical procedures or can be made by further treatment of the extract from rabbit medulla described in the aforementioned copending application Ser. No. 931,859 filed Aug. 7, 1978, which is hereby incorporated by reference.

The compounds of this invention may be prepared from mammalian kidney medulla such as, for example, isolated rabbit medulla as follows. The rabbit medulla is removed from a slaughtered rabbit, and is homegnized and incubated, e.g., from 10 minutes to 2 hrs. at about 25° to 40° C. and most preferably 37° C., approximately the body temperature of the rabbit, for a time sufficient to permit the medulla to produce a substance which, after lipid extraction, produces a yellow oil. Thereafter, the yellow oil is reduced, acylated, passed through a silicic acid column and then purified through twice using thin layer chromatography to provide an ARL composition.

It has been found that without the incubation step amounts of material obtained from the medulla are not sufficient or cannot be detected to produce the desired end product, i.e., the ARL compound since the material which is needed to produce the ARL compound appears not to be available if conditions are not acceptable within the medulla after the medulla is removed from the body and not held under proper temperature and conditions for a sufficient time after removal from the body of the animal (rabbit).

The above composition from treated medulla extract has been found to be a mixture containing a polar fragment of α-ester phospholipids and α-ether phospholipids. The alpha and beta esters of the ARL compound can be hydrolyzed to the corresponding acids without affecting the ether groups by use of phosholipases that selectively reduce each ester. Two products are obtained by separation: α-OH, β-OH phspholipid and α-ether, β-OH phospholipid. These products can be used as intermediates to produce the compounds of this invention. Standard chemical reactions can be used to esterfy the products using readily available fatty acids and the ether group can be changed by other well known reactions. Phospholipase $A_2$ can be used to selectively remove ester substituents at the β carbon and pancreatic lipases (phospholipase $A_1$) can be used to selectively remove ester substituents at the α carbon so that the desired ester can be attached.

The $R^1$ substituent at the α carbon can have from about 11 to about 23 carbon atoms, preferably 13 to 19 carbon atoms and most preferably 15 to 17 carbon atoms. Preferably the $R^1$ substituent can be saturated or can have one or more carbon-carbon double bonds, preferably one or two double bonds.

The $R^2$ substituent at the β carbon can be hydrogen or have from 1 to about 11 carbon atoms preferably 1 to 4 carbon atoms. Most preferably $R^1$ is methyl, i.e. the substituent at the β carbon is acetoxy.

The $R^3$ substituent can be an amine, substituted amine, an ammonium group or substituted ammonium group wherein the substituents are lower alkyl groups having from 1 to about 3 carbon atoms. When $R^3$ is an ammonium group there is an anion associated with it that can be any anion such as, for example, hydroxides, chlorides, and the like. Preferred $R^3$ substituents are unsubstituted amine and trimethylammonium hydroxide.

Examples of compounds in accord with the present invention include:

phosphoric acid (2-acetoxy-3-hexadecyloxy propyl)-2-aminoethyl ester phosphoric acid (2-acetoxy-3-hexadecyloxy propyl)-[(N-2-ethyl0 trimethylammonium hydroxide]ester phosphoric acid [2-acetoxy-(3-hexadec-en-oxy)propyl]-2-aminoethyl ester phosphoric acid [2-acetoxy-(3-hexadec-en-oxy) propyl]-[(N-2-ethyl)trimethylammonium hydroxide]ester phosphoric acid (2-acetoxy-3-heptadecyloxy propyl)-2-aminoethyl ester phosphoric acid (2-acetoxy-3-heptadecyloxy propyl)-[N-2-ethyl)trimethylammonium hydroxide]ester phosphoric acid [2-acetoxy-(3-heptadec-en-oxy)-propyl]-2-aminoethyl ester phosphoric acid [2-acetoxy-(3-heptadec-en-oxy)-propyl]-[(N-2-ethyl)trimethylammonium hydroxide]-ester phosphoric acid (2-acetoxy-3-octadecyloxy propyl)-2-aminoethyl ester phosphoric acid(2-acetoxy-3-octadecyloxy propyl)-[(N-2-ethyl)trimethylammonium hydroxide]ester phosphoric acid [2-acetoxy-(3-octadec-en-oxy)propyl]-2-aminoethyl ester phosphoric acid [2-acetoxy-(3-octadec-en-oxy)propyl]-[(N-2-ethyl)trimethylammonium hydroxide]ester phosphoric acid (2-acetoxy-3-palmitoyloxy propyl)-2-aminoethyl ester phosphoric acid (2-acetoxy-3-palmitoyloxy propyl)-[(N-2-ethyl)trimethylammonium hydroxide]ester phosphoric acid (2-acetoxy-3-heptadecanoyloxy propyl)-2-aminoethyl ester phosphoric acid (2-acetoxy-3-heptadecanoyloxy propyl)-[(N-2-ethyl)trimethylammonium)hydroxide]-ester phosphoric acid (2-acetoxy-3-stearoyloxy propyl)-2-aminoethyl ester phosphoric acid (2-acetoxy-3-stearoyloxy propyl)-[(N-2-ethyl)trimethylammonium hydroxide]ester phosphoric acid (2-acetoxy-3-oleoyloxy propyl)-2-aminoethyl ester phosphoric acid (2-acetoxy-3-oleoyloxy propyl)-[(N-2-ethyl)trimethylammonium hydroxide]ester The compounds of this invention are antihypertensive when injected intravenously or when given by mouth. The antihypertensive effect has been tested in hypertensive rats. The antihypertensive effect proceeds in several ways depending on the method of introduction into the body and the dose.

When injected intravenously as a bolus dose into hypertensive recipients, these compounds cause an acute depressor effect, lowering the arterial pressure rapidly by causing dilation of resistance blood vessels (small arteries and arterioles). When given as an infusion intravenously, they lower the arterial pressure quickly and by titrating the dose input, the arterial pressure can be set at various levels. In larger doses or in multiple doses, intravenously or by mouth, these compounds cause a prolonged depressor effect, the arterial pressure remains depressed for 24 hours or more beyond the last input of the compound. This latter approach is capable of controlling hypertension in a continuous fashion.

Treatment of mammals such as rats, dogs, rabbits, cats, humans for any of the aforementioned conditions can be accomplished by administering a treatment effective amount of an anti-hypertensive compound of the invention. Conveniently a dose in the range of from 5 to about 90 micrograms/kg body weight is administered. A single dose of about 15–20 micrograms/kg is administered intravenously to achieve acute vasodilatation or treat cardiogenic shock. The compounds are preferably administered twice daily intravenously at a dose in the range of 18 to about 25 micrograms/kg or orally at a dose of about 60 micrograms/kg to produce a powerful antihypertensive action of the prolonged type.

When treating a mammal for hypertension, a dosage preferably to 30 to 50 micrograms/kg is administered intravenously twice daily for two days and thereafter, a maintenance dose of 20 micrograms/kg of body weight is administered daily. Thus, a unit dose of the compound in humans would be 2 mg to 5 mg. Presently the alkyl ether compounds of this invention are preferred.

Compounds of this invention are preferably administered parenterally or orally and less preferably, as a suppository in a pharmaceutically acceptable carrier. Most preferably, the compounds are injected in a suitable pharmaceutically acceptable vehicle in solution into a vein (I.V.); however, they can be injected into an artery, into muscle, i.e., intramuscularly, or subcutaneously, or may be infused I.V. in saline or Ringer's solution. The administration of the compounds of this invention will, of course, be accomplished in accordance with the physician's instructions and the actual dose used will be based on the observations and discretion of the physician. The mode of administration will be selected by the physician in attendance; however, best results to date have been with the parenteral I.V. injections using a single dose bolus or a multidose vial from which single doses of a compound of the invention in solution in a pharmaceutically acceptable carrier are withdrawn. The compositions for injection must, of course, be sterile and desirably isotonic with the blood of the mammal into which they are being administered.

A suitable diluent is 2% saline and, in addition, solubilizing additives such as albumin or lecithin may be added. Advantageously, the compounds of the invention are suspended dissolved in a sterile diluent under aseptic conditions. Sterilization of the injection compositions may be effected by conventional techniques. In addition, injectable preparations may be made by adding sterile water to a tube containing the compound as a solid to form a unit dose or a multi-dose. Also the compound as a solid may be compounded into tablet form.

The present invention will be further illustrated by the examples that follow. The examples are solely for illustration and are not intended to limit the scope of the invention.

EXAMPLE 1

A very active preparation of ARL was obtained from rabbit renal medulla according to the following seven step procedure:

Step I Incubation

New Zealand White rabbits were fasted for 40-44 hours with water ad libitum. They were then stunned by a blow on the head and decapitated. The kidneys were removed and placed in wet ice within 10-15 minutes of sacrifice, and the medullas were dissected out as rapidly as possible. To 125 g. of fresh medullas (from approximately 104 kidneys) in a one liter glass Waring Blendor cup were added 0.268 M Sorensen's phosphate buffer, pH 7.5 (125 ml), and the mixture was blended for 15 seconds at low speed and then for 2 minutes at high speed. The resulting homogenate was transferred to a 1200 ml Virtis flask and washed into the flask with sterile saline (125 ml). The homogenate was incubated for 32 minutes in a 37° C. water bath with frequent swirling. The incubated homogenate was then frozen and freeze-dried.

Step II Lipid Extraction

The lyophilized tissue powder was extracted by the Bligh and Dyer method [*Can. J. Biochem. and Physiol.*, 37, 911 (1959)] as follows:

Water was added to give a mixture containing 80% water. Then chloroform and methanol were added to give a final solvent ratio of chloroform:methanol:water equal to 1:2:0.8. The mixture was then blended at fast speed for two minutes. Further additions of chloroform and of water, with 30 seconds of blending after each addition, gave a final solvent ratio of chloroform:methanol:water equal to 2:2:1.8. Centrifugation in a Sorvall RC 2B centrifuge (40 minutes at 5000 rpm) separated an aqueous layer (discarded) and a chloroform layer, which was drawn off and saved. The solids at the water: chloroform interface were resuspended in chloroform (1.5 volumes), blended for 30 seconds at low speed, and the mixture centrifuged 40 minutes at 5000 rpm. The chloroform layer was pooled with the above saved chloroform layer. The combined chloroform solution was evaporated under reduced pressure. Chloroform was added to the residue and evaporated under reduced pressure to remove traces of water, leaving a yellow oil (6.5 g).

Step III Vitride Reduction

The residual yellow oil from Step II was dissolved in 54.1 ml of a mixture of ethyl ether:benzene (80:20). The glass stoppered flask containing the yellow solution was swirled in cool running tap water as 10.58 ml of Vitride were added. (Vitride is a 70% solution of sodium bis (2-methoxy-ethoxy) aluminum hydride in benzene.) The volume used represents 7.40 gms of the latter. A vigorous reaction ensued during the early part of the addition, but the cooling water kept it under control. The glass stopper was taped in and the flask was incubated. with occasional swirling, at 37° C. for 32 min. The flask was opened and the addition of a few drops of 4% acetic acid caused a vigorous reaction, indicating that an excess of reagent was present. Addition of a total of 129.2 ml of 4% acetic acid, cooling the flask under tap water, caused the appearance of a white gelatinous precipitate.

This suspension was extracted four times in a separatory funnel with 100 ml of ethyl ether each time. The emulsion was centrifuged 15 minutes, 2100 rpm, at 5° C. and the other layer drawn off each time, pooled, and taken to dryness under reduced pressure. The aqueous layer above was re-extracted two times with 100 ml chloroform, and the chloroform layers obtained after centrifugation were pooled and taken to dryness under reduced pressure in the flask containing the ether extract. A final 100 ml of chloroform were added and distilled off to ensure removal of the last of the water. There resulted 5.4 gm of clear second yellow oil.

Step IV Acetylation

The 5.4 gm of clear yellow oil above were dissolved in 6.6 ml of pyridine (redistilled A R grade stored over KOH pellets). Addition of 26.2 ml of A R grade acetic anhydride caused some turbidity. Incubation at 45° C. for 32 min., with occasional swirling, followed.

This was followed by removal of pyridine and excess acetic anhydride by distillation under reduced pressure 40° C. A final heating to 65° C. with nitrogen blowing into the flask for a short time removed practically all of the acetic anhydride. The acetylated fatty alcohols resulting, a cloudy yellow oil, weighed 5.8 grams.

Step V Column Chromatography

A 1×30 cm column was packed with silicic acid (9.0 g, Unisil®, 100–200 mesh, acid washed, obtained from Clarkson Chemical Company, Inc., Williamsport, Pa.), suspended in chloroform. The cloudy yellow oil from Step IV was dissolved in 40 ml of the bottom phase from the solvent mixture chloroform:methanol containing 2% acetic acid:water (1:1:1), which bottom phase had been clarified by centrifugation. The solution of the cloudy yellow oil was also clarified by centrifugation and then placed on the column. The flow rate was adjusted to 3 drops every 5–7 seconds. When the solution had entered the column, a wash (50 ml) of the clarified bottom phase was added; and 5 minute fractions were collected. The ARL compound was eluted with chloroform:methanol:acetic acid:water (50:25:8:4) with the flow rate maintained at 3 drops every 5–7 seconds and 5 minute fractions collected. Using this system the active ARL compound generally first appears in fractions 15–20 and is detected by assay. The volume of each fraction was 4–5 ml and a 20 µl aliquot was taken from each for assay.

The assay was performed by evaporating the aliquot solvent to dryness under a nitrogen stream, suspending with sonication the residue in 0.3 ml of saline containing 1 µg/ml lecithin, injecting the suspension intravenously into a one-kidney Goldblatt hypertensive rat, and monitoring the change in blood pressure in the rat.

The active fractions were combined and evaporated to dryness under a nitrogen stream in a 50° C. water bath to give a third yellow oil (14.3 mg).

Step VI Thin Layer Chromatography TLC 1

TLC plates were prepared using double strength window pane glass (5×20 and 20×20 cm) and silica gel MN-Kieselgel G-HR (Brinkmann Instrument, Inc., Cantiagne Rd., Westbury, N.Y.). The plates were layered with the silica gel 0.25 mm thick, allowed to stand at room temperature 30–45 min., and activated at 110° C. for one hour. They were stored prior to use in a cabinet containing a dessicant.

Each plate was marked 2.5 cm from the bottom edge and 10 cm above the first mark. The third yellow oil from Step V was dissolved in 450 µl of chloroform. The solution was then spotted (8 µl) onto one guide plate (5×20 cm) and the rest streaked evenly across three 20×20 cm plates. The TLC plates were developed in a paper-lined chromatography jar containing chloroform:methanol:acetic acid:water (50:25:8:3) about 1–2 cm deep until the solvent front reached the 10 cm mark. They were then removed and air dried. The guide plate was sprayed with concentrated sulfuric acid and heated to char. Based on the chared pattern obtained with the wide plate, the 20×20 cm plate were cut into four fractions: no. 1, from 0.5 cm before to 0.5 cm beyond the origin; no. 2, from 0.5 cm to 1.7 cm beyond the origin; no. 3, from 1.7 cm to 3.0 cm beyond the origin; and no. 4, from 3.0 cm to 10.0 cm beyond the origin. Each fraction was scraped into a 50 ml centrifugation tube and eluted as follows: water (7 ml) was added to each tube and mixed thoroughly; methanol containing 2% acetic acid (14 ml) was added and shaken; chloroform (14 ml) was added and shaken for 5 minutes; and finally, water (7 ml) was added and shaken for 5 minutes. The tubes were centrifuged at 2000 rpm for about 10 minutes at 20° C. to separate the phases. The chloroform layers were removed and evaporated to dryness under a nitrogen stream. Each fraction was redissolved in chloroform (2.0 ml) and assayed as above. The antihypertensive activity was found to be concentrated in the no. 2 fraction, a fourth yellow oil (0.7 mg).

Step VII TLC 2

The fourth yellow oil from Step VI was subjected to thin layer chromatography according to the procedure of Step VI except one guide plate (5×20 cm) and one 20×20 cm plate were used and the developing solution was chloroform:methanol:concentrated aqueous ammonia (75:25:4). The activity was concentrated in a band from 0.5 to 1.6 cm beyond the origin, and the final yield of a light yellow oil ARL in 0.18 mg.

EXAMPLE 2

Infusion of ARL

A 0.2% solution of rat albumin (rat albumin, fraction V, Sigma #A-4760) in saline (0.9% saline, Cutter Laboratories) was sterilized by filtration through a 0.45 micron filter (Nolge #245-0045) and stored in a sterile multiple use vial at 0°–4° C. Immediately prior to administration, the albumin solution (1.0 ml) was added to a 12×75 mm tube containing 100 µg of the light yellow oil ARL of Example 1. Suspension of the ARL was effected by swirling the tube in an ultrasonic bath for 30 seconds. The resulting suspension was infused into a Goldblatt one-kidney hypertensive rat weighing 300 g over an 8 hr. period, i.e., at a rate of 0.125 ml/hr for the suspension (12.5 µg/hr of the light yellow oil ARL preparation). A decrease in the blood pressure was measured.

EXAMPLE 3

Bolus Administration

A suspension (0.075 ml) of light yellow oil ARL in saline prepared according to Example 2 was administered to a Goldblatt one-kidney hypertensive rat weighing 300 g by intravenous injection. An immediate, sharp drop in blood pressure of about 60% occurred within less than one minute after administration.

EXAMPLE 4

Effect of Continuous Administration Of ARL to Hypertensive Rats

The test animals were Goldblatt hypertensive rats. Each animal had a stable blood pressure in the range of 160–200 mm Hg approximately one month post preparation. Approximately one to two weeks prior to test the animals were prepared with chronic indwelling catheters for injecting intravenously and for measuring mean arterial blood pressure. Five animals were used for the treated group and five were used for controls. The vehicle was 0.2% rat albumin dissolved in saline. A 100 µg dose of ARL (two dimensional thin layer chromatography material) was solubilized in 1.0 ml of the vehicle and given intravenously by continuous infusion to each treated rat for 8 hours (125 µl/hr). The controls were given vehicle only. The mean arterial blood pressure was monitored before and for 5 min. every 30 minutes during the 8 hour test period. The blood pressure of the treated animals decreased to near 100 mm Hg and remained at that level during the continuous infusion. The control animals remained at their pre-level during this same period. The animals were then returned to their home cages overnight and the next day their blood pressure was measured prior to giving the second continuous infusion for 8 hours. The treated group had a lower blood pressure at 24 hr. post start of the infusion and also at 48 hrs. past. The blood pressures were usually depressed 30–50 mm Hg over the pre-pressures at the 48 hr reading.

EXAMPLE 5

Effect of Injecting ARL as a Bolus

The experimental animals were Goldblatt hypertensive rats prepared as given in above example. The vehicle for this experiment was either 0.2% rat albumin or 1 mg/ml lecithin in saline. A 50 µg dose of ARL (two dimensional thin layer chromatographed material) was solubilized in 0.3 ml of the vehicle by sonication. Then after measuring the pre-mean arterial pressure, the five experimental rats were injected intravenously as a bolus small amounts until the 0.3 ml was given, being careful to maintain the blood pressure above 50 mm Hg. The five control animals were injected with the vehicle only. This same dose was administered again about 4 hours after the first dose. The rats were then returned to their home cages. The next day the above dosing of the animals was repeated. The mean arterial pressure taken at 24 hours, just prior to the third, and again at 48 hrs past first dose were generally 30–50 mm Hg below the pre-pressures while the controls remained unchanged.

EXAMPLE 6

In each of the following experiments, vehicle for ARL (made as per Example 1) was L-α-Lecithin (Di-palmitoyl) 1 mg/ml, Grand Island Biological Co., U.S.A. The ARL (the product of Example 1) was first dissolved in chloroform to facilitate removal of known amounts and after evaporating the solvent with a stream of nitrogen ARL was redissolved in Lecithin using an ultrasonic vibrator.

Direction of responses indicated by arrows. All values are approximate to mean.

↑—increase, ↓—decrease, 0—no change.

1. Rats (a) Unanesthetized Genetic Hypertensive
Method
Sex: male; weight: 320–340 g; strain: New Zealand.
Pulsatile blood pressure measured directly by indwelling caudal artery catheter. Integrated heart rate recorded using tachometer triggered by arterial pressure waves. Drug injection via cannulated left jugular vein or oral.
Result
(i) Intravenous injection (in 0.1–0.2 ml), n=4.
Mean initial systolic blood pressure (±S.E.M.): 171±4 mm Hg.
Mean initial diastolic blood pressure (±S.E.M.): 118±6 mm Hg.
Mean initial heart rate (±S.E.M.): 429±18 beats/min.

| ARL µg/kg i.v. | Mean fall in BP (± S.E.M.) | | Mean duration of hypotension (min) (± S.E.M.) | Mean (± SEM) tachycardia (beats/min) |
|---|---|---|---|---|
| | Systolic (mm Hg) | Diastolic (mm Hg) | | |
| 0.4 | 48 ± 2 | 35 ± 5 | 0.8 ± 0.5 | 3 ± 3 |
| 0.8 | 85 ± 6 | 49 ± 6 | 2.2 ± 0.2 | 3 ± 3 |
| 1.5 | 113 ± 5 | 68 ± 7 | 4.7 ± 1.2 | 0 |
| 3.0 | 117 ± 7 | 68 ± 2 | 7.9 ± 0.7 | 4 ± 4 |
| 6.0 | 119 ± 12 | 74 ± 6 | 12.8 ± 0.9 | 9 ± 5 |
| Vehicle (0.4 ml) | 0 | 0 | 0 | 0 |
| 12 µg/kg i.v. | 106 ± 16 | 68 ± 5 | 13.0 ± 1.1 | 3 ± 3 |

(ii) Intravenous infusion, n=2.
Mean initial blood pressure: (Systolic/diastolic 213/123 mm Hg).
Mean initial heart rate: 414 beats/min.

| ARL µg/kg/min | Fall in systolic BP (mmHg) | Fall in diastolic BP (mmHg) | Change in Heart rate (beats/min) |
|---|---|---|---|
| 0.12 | 8 | 5 | 0 |
| 0.3 | 38 | 20 | 0 |
| 0.6 | 38 | 30 | 0 |
| 1.2 | 55 | 38 | 0 |

Hypotension sustained during infusion.
Conclusions
Hypotension followed intravenous administration, the effect involving both systolic and diastolic blood pressure. At the same time the heart rate was not importantly altered by ARL.
(b) Anesthetized
(i) Normotensive. N=2.
Method
Sex: male; mean weight: 300 g; strain: New Zealand Otago Wistar.
Anesthetic: initially chloroform, then maintained by intravenous chloralose 70 mg/kg.
ARL injected into left femoral vein (i.v.).
Blood pressure measured directly from left femoral artery.
Heart rate recorded using tachometer triggered by arterial pressure waves.
Result

| Drug i.v. (µg/kg) | Change in Systolic BP mm Hg | Change in Diastolic BP mm Hg | Duration of hypotension (min) | Change in Heart rate (beats/min) |
|---|---|---|---|---|
| Vehicle (0.4 ml) | 0 | 0 | 0 | 0 |
| ARL | | | | |
| 0.38 | ↓ 50 | ↓ 35 | 1.5 | ↑ 18 |
| 0.75 | ↓ 75 | ↓ 47 | 1.5 | ↑ 30 |
| 1.5 | ↓ 60 | ↓ 55 | 4.0 | ↑ 24 |
| 3.0 | ↓ 78 | ↓ 60 | 7.5 | ↑ 24 |
| 6.0 | ↓ 95 | ↓ 55 | 21.0 | ↑ 36 |
| 12.0 | ↓ 113 | ↓ 66 | 24.0 | ↑ 30 then ↓ 36 |

(ii) Genetic hypertensive n=2.
Method
Sex: male, mean weight approx. 300 g; strain: New Zealand.
Anesthetic: initially chloroform subsequent maintenance with intravenous chloralose 60–70 mg/kg.
ARL injected into left femoral vein.

Blood pressure recorded directly from left femoral artery.
Heart rate recorded using tachometer triggered by arterial pressure waves.

| Drug i.v. (μg/kg) | Change in Systolic BP mm Hg | Change in Diastolic BP mm Hg | Duration of hypotension (min) | Change in Heart rate (beats/min) |
|---|---|---|---|---|
| Vehicle | 0 | 0 | 0 | 0 |
| ARL |  |  |  |  |
| 0.38 | ↓68 | ↓55 | 3.0 | 0 |
| 0.75 | ↓75 | ↓60 | 6.3 | ↓24 |
| 1.5 | ↓120 | ↓80 | 8.6 | ↑30 |
| 3.0 | ↓160 | ↓100 | 13.8 | ↓48 |
| 6.0 | ↓195 | ↓120 | 22.3 | ↓48 |
| 12.0 | ↓205 | ↓125 | >42.0 | ↓78 |

Conclusion

Hypotension occurred in normotensive and hypertensive anesthetized rats after intravenous injections of ARL. Responses of the heart rates were variable; bradycardia being the usual effect in hypertensives whereas normotensives responded with tachycardia.

(c) Pithed. n=3.
Method
Sex: male; weight: 250-300 g; strain: New Zealand Otago Wistar.
Preparation: Gillespie, MacLaren and Pollock (1970) Br. J. Pharmac. 40, 257.
Pithing rod used as an electrode for electrical stimulation of the cardiac nerves. Blood pressure recorded from left femoral artery, heart rate by tachometer. Shocks of Supramax. voltage, 0.25 Hz; 2 msec width:—Response of ↑138 beats/min sustained tachycardia.
Result
Effect of ARL on tachycardia to preganglionic nerve stimulation

| Drug (μg/kg) | Heart rate (beats/min) | Changes in Mean Blood Pressure (mmHg) |
|---|---|---|
| 0.38 | 0 | ↓15 |
| 0.75 | 0 | ↓15 |
| 1.5 | 0 | ↓15 |
| 3.0 | ↓6 | ↓20 |
| 6.0 | ↓18 | ↓15 |
| 12.0 | — | ↓15 |

Initial findings indicate pressor responses to noradrenaline or angiotensin II were unaffected.

Conclusion

No major effect on the tachycardia produced by indirect stimulation. Hypotension followed intravenous injections of ARL.

2. Rabbits (1) Intravenous (i.v.) or Intra-arterial (i.a.) injection n=1.
Method
Sex: female; strain: New Zealand White; weight: 2.2 kg.
Anesthesia: Urethane (1.5 g/kg) into the ear vein.
Blood pressure measured from femoral artery.
Heart rate recorded using tachometer triggered by arterial pressure waves.
Drug injected into femoral vein or retrogradely into carotid artery.
Result
Initial blood pressure: 140/72 (Systolic/diastolic mmHg).
Initial heart rate: 320 (Beats/min).

| Drug (μg/kg) | Change in Systolic BP (mmHg) i.v. | i.a. | Change in Diastolic BP (mmHg) i.v. | i.a. | Change in Heart rate (Beats/min) i.v. | i.a. |
|---|---|---|---|---|---|---|
| Vehicle | 0 | 0 | 0 | 0 | 0 | 0 |
| ARL |  |  |  |  |  |  |
| 0.06 | ↓19 | ↓7 | ↓16 | ↓6 | ↓8 | 0 |
| 0.1 | ↓36 | ↓13 | ↓32 | ↓12 | ↓15 | 0 |
| 0.2 | ↓40 | ↓18 | ↓40 | ↓21 | ↓55 | 0 |
| 0.5 | ↓42 | ↓27 | ↓37 | ↓24 | ↓53 | ↓10 |
| 0.9 | ↓43 | ↓29 | ↓38 | ↓28 | ↓55 | ↓40 |

(2) Intra-renal artery. n=2.
Method
Sex: male; weight: 2.5 kg; strain: New Zealand White.
Anesthesia: initially Halothane, then i.v. chloralose (40 mg/kg and pentobarbitone sodium 2 mg/kg).
Blood pressure recorded from left femoral artery.
Heart rate recorded using tachometer triggered from arterial pressure wave.
Central venous pressure (CVP) via jugular vein.
Left renal blood flow using electromagnetic flowprobe.
Drug administered by infusion retrogradely into suprarenal artery.
Result

| Drug (μg/kg/min) | Change in Diastolic BP (mmHg) | Change in Heart rate (beats/min) | Change in Renal blood flow (ml/min) % | Change in CVP (mmHg) |
|---|---|---|---|---|
| Vehicle | 0 | 0 | 0 | 0 |
| ARL |  |  |  |  |
| 0.16 | 0 | 0 | ↓25 | 0 |
| 0.4 | 0 | 0 | ↓50 | 0 |
| 0.8 | ↓10 | 0 | ↓70 | 0 |
| 1.6 | ↓10 | 0 | ↓80 | 0 |
| PGE$_2$ |  |  |  |  |
| 0.4 | 0 | 0 | ↑20 | 0 |
| PGX |  |  |  |  |
| 0.4 | 0 | 0 | ↑18 | 0 |

(3) Intravenous infusion—after (2) above

| Drug (μg/kg/min) | Change in Systolic BP (mmHg) | Change in Diastolic BP (mmHg) | Change in Heart rate (beats/min) | Change in Renal blood Flow (ml/min) % | Change in CVP (mmHg) |
|---|---|---|---|---|---|
| Vehicle | 0 | 0 | 0 | 0 | 0 |
| ARL |  |  |  |  |  |
| 0.4 | ↓15 | ↓10 | 0 | ↓20 | 0 |
| 0.8 | ↓15 | ↓10 | 0 | ↓66 | 0 |
| 1.6 | ↓20 | ↓10 | ↑18 | ↓100 | 0 |

Conclusion

Hypotension and bradycardia followed either intravenous or intra-arterial injections of ARL, the effect being greater intravenously. Renal blood flow was reduced after administration by either route.

3. Dog n=1
Method
Sex: female; weight; 15 kg; strain: Labrador.
Anesthesia: chloralose (50 mg/kg) and pentobarbitone sodium (15 mg/kg).

Injections either intravenous or intra-renal arterially (IV or IRA).
Blood pressure recorded from brachial artery.
Central venous pressure (CVP) measured from a catheterized jugular vein.
Renal blood flow (RBF) measured using an electromagnetic flow probe placed around the left renal artery.
Assay tissue—dog blood superfused. Dog portal vein, DPV; rabbit aorta, RA; chick rectum, CR; rat colon, RC.
Result

| | | |
|---|---|---|
| 1 | ARL (1.25 μg/kg i.v. = 20 μg) caused | (a) slight ↓ BP |
| | | (b) slight ↓ CVP |
| | | (c) slight ↓ RBF |
| 2 | ARL (1 to 20 μg IRA) caused | (a) slight ↓ BP |
| | | (b) slight ↓ CVP (delayed) |
| | | (c) slight ↓ RBF |
| 3 | ARL (0.1 to 1 μg over assay tissues) caused | (a) ↑ tone DPV |
| | | (b) ↑ tone RA |
| | | (c) no change CR |
| | | (d) ↑ tone RC |

Conclusion
Hypotension and reduced renal blood flow after ARL.

4. Guinea Pig—Respiratory studies (1) Airway resistance and dynamic compliance.
Method
Sex: female; weight: 500 g; strain: Redfern.
Anesthesia: Urethane 7.2 g/kg.
Recorded variables—airways resistance (computed from pressure difference at isovolumetric points divided by flow rate difference at isovolumetric points) Dynamic compliance (Tidal volume/Pleural pressure).
Carotid blood pressure.
Injections made into femoral vein.
Result

| | | | Change in Blood Pressure (mmHg) | |
|---|---|---|---|---|
| Drug (μg/kg) | Change in airway resistance | Change in Compliance | Systolic | Diastolic |
| 1 | ↑ 50% | ↓ 40% | ↓ 30 | ↓ 11 |

Threshold for hypotension approximately 0.05–0.1 μg/kg.
Threshold for increased airway resistance 1.0–3.0 μg/kg.

(2) Inflation Pressure. n=2
Method
Dixon and Brody (1903). J. Physiol 29, 97.
Pithed guinea pig. Sex: male; weight: 500 g; strain: Redfern
Blood pressure recorded from carotid artery.
Inflation pressure recorded from trachea.

| Drug (μg/kg) | Change in Inflation Pressure | Change in Systolic BP (mmHg) | Change in Diastolic BP (mmHg) | Change in Heart rate (Beats/min) |
|---|---|---|---|---|
| Vehicle | 0 | 0 | 0 | 0 |
| ARL i.v. | | | | |
| 0.1 | 0 | 0 | 0 | 0 |
| 0.3 | ↑ 3 | ↓ 3 | ↓ 3 | 0 |
| 1.0 | ↑ 70 | ↓ 22 | ↓ 12 | — |
| Histamine i.v. | | | | |
| 5.0 | ↑ 50 | ↑ 12 | ↑ 3 | ↑ 12 |

Response to histamine potentiated by ARL.

(3) Superfused isolated tracheal rings
Result
ARL 10 μg: NO EFFECT (Usual contraction to PGF$_{2\alpha}$).
Conclusion
Increased airway resistance accompanied by hypotension produced by ARL. Some evidence that a lower dose is required for a threshold hypotensive effect. Constriction of pulmonary vessels could contribute to reduced compliance. Tracheal smooth muscle was unaffected in vitro.

5. Superfusion of Isolated Tissues—in vitro ( ↑ Contraction; ↓ relaxation).
(0 No change)

| Response to ARL (up to 5 μg applied directly over tissue) | |
|---|---|
| Rat Colon | ↑ (prolonged, 100–200 ng) |
| Chick Rectum | 0 |
| Rat Stomach Strip | ↑ (prolonged, 100–200 ng) |
| Guinea Pig Ileum | 0 |
| Rabbit Mesenteric artery strip | 0 |
| Rabbit Coeliac artery strip | 0 |
| Rabbit Femoral artery strip | 0 |
| Rabbit Prox vena cava | 0 |
| Rabbit coronary artery | ↓ (100–200 ng) |

Tissue respond normally to standards, e.g., PGE$_2$ (10 ng) or SRS-A (1–2 units).
Conclusion
Contraction of rat colon and stomach strip non-vascular smooth muscle. Rabbit coronary artery relaxed but other vessels unaffected.

6. Spontaneously beating atria—in vitro

Method n=3
Guinea pig, weight: 500–615 g; strain: Redfern; sex: female.
Applied tension 1 g.
35° C. Krebs solution.
Result
Vehicle—no effect on force or rate of contraction.
ARL μg/ml 0.01–4 no effect on force or rate of contraction.
Conclusion
No important effects on force or frequency of arterial contraction.

The polar nature of the product of Example 1 is indicated by its behavior on TLC and its solubility in water. The structural formula of the active compounds was determined by using standard chemical analysis procedures including:

alkaline and acid hydrolysis (acid treat, 50–500 μg lipid/ml of 0.1N HCl, 30 minutes at 60° and 80° C.; alkaline treatment, 50 μg lipid/ml of 0.1N NaOH 30 minutes at 60° C.); treatment with phopholipases A$_1$, A2, C and D (Lowenstein Methods in Enzymology, Academic Press, Inc. New York, 1969); reduction with palladium on charcoal plus H$_2$ (1 mg lipid in 100 mg Pd on charcoal plus bubbling H$_2$ for 5–10 minutes, one hour at room temperature with occasion swirling); treatment with mold lipase (Rhizopus delemar; Slotboom et at, *Chem. Phys. Lipids* 4: 15–29, 1970); repeat treatment with the Vitrade reagent; treatment with HgCl$_2$-glacial acetic acid (1 mg lipid/5 ml 1% HgCl$_2$ in glacial acetic acid 30 minutes at 46° C.); and determination of the phosphorous:nitrogen ratio (Galbraith Laboratories, Knoxville, Tenn.).

In the examples that follow, the product of Example 1 will be referred to as APRL.

EXAMPLE 7

A. Acute Depressor Effect

Wister rats obtained from the Bio-Lab Corporation, St. Paul, Minn., and weighing about 250 gm were used. The 1KGH was induced as previously described (Brooks et al, *Arch Path* 93: 116–117, 1972). Three months later these animals were utilized to evaluate APRL. The presence of sustained hypertension for this time was determined by the tail-cuff method using the E and M apparatus. Anesthesia was induced in seven 1KGH rats by 2% α-chloralose and 10% urethane at a dose of 6 ml/kg. The left carotid artery was cannulated with PE 50 tubing for measurement of the arterial pressure using a Statham P 23 Gb strain gauge. The right external jugular vein was cannulated for the injection of APRL. In two animals the central venous pressure was measured with a Statham P 23 BB strain gauge. The trachea was cannulated and connected to a Harvard model 680 rodent respirator with the rate set at 70 breaths/min and tidal volume set at a minimum to prevent voluntary ventilation. A midline thoracotomy was performed and the pericardium was opened. A 2 mm Statham flow probe was placed on the root of the aorta to measure cardiac output (CO) using a Statham flowmeter, model SP 2202. The flowmeter and probe were precalibrated on the in situ brachial artery of a dog by withdrawing blood from the artery at constant rates with a Sage infusion/withdrawal pump. The mean instantaneous blood flow and the acceleration of blood flow were recorded. The peak acceleration of blood flow divided by the peak instantaneous blood flow was used as an index of myocardial contractility (Nutter et al, 1971). All recordings were made on a Brush model 200 oscillograph. Doses of 0.01 to 1.0 μg of APRL were injected through the venous cannula after being made up in saline by 30 second sonication. The APRL was given in ascending followed by descending doses in 0.1 ml, or vice versa, so that every dose was given twice.

Characteristics of the acute depressor effect of APRL will be described below.

The interval between initiation of the bolus dose to the start of the sharp drop of the MAP was $3.8\pm0.2$ seconds (n=10). The time for the sharp drop to reach its maximum was $10.8\pm0.5$ seconds (n=10). A high dose is indicated in FIG. 1 by the floor of the MAP (~75 mm Hg) lasting about six minutes. Thereafter, the pressure recovered slowly and completely by 50 minutes.

The pulse rate before the injection averaged $405\pm5$ beats/minute (n=10). At maximum depression ($-94\pm8$ mmHg) it averaged $438\pm6$ beats/minute (n=10, $p<0.001$). By two minutes after the maximum depression the rate had decreased to $423\pm3$ beats/minute (n=10, vs before injection $p<0.01$) and at four minutes following the injection, the rate had recovered to $405\pm5$ (n=8, vs before injection $p>0.9$). Thus, despite the substantial acute depressor effect, tachycardia was at a minimum and recovered rapidly despite the persistent depression of MAP. During the time of the depressor effect the animals appeared alert, responding normally to abrupt provocation by a blunt instrument.

Hemodynamic features of the acute depressor effect of APRL are as follows. The prethoracotomy MPA of the anesthetized one-kidney, hypertensive rats was $147\pm5.2$ mmHg, and this was reduced to $128\cong8$ mmHg after completion of the surgery. Although blood loss was minimal, the CI seen under these conditions was reduced from the unanesthetized values shown in table 2. This is a common finding for open chest animals (Fermoso et al, *Am. J. Physiol*, 207: 1112–1116, 1964). Upon injection of APRL there was an immediate, dose dependent fall in blood pressure and a slightly delayed fall in cardiac output which was very small at low doses and increased at the two highest doses. The heart rate on this record showed a decline during the hypotensive period at the 1 μg dose, but in most of the experiments the heart rate did not change. The heart rate was $388\pm5.9$ beats/min before the injection of 1.0 μg of APRL and $384\pm6.5$ beats/min during the hypotensive period (not significant or NS). The peak acceleration of blood flow and the peak instantaneous blood flow decreased by similar proportions, thus giving no significant change in the contractility index of the myocardium (peak acceleration of blood flow/peak instantaneous blood flow). The index of contractility was $100\pm2.4$ sec.$^{-1}$ during the control period and $96\pm1.2$ sec$^{-1}$ during the hypotensive period after the 1.0 μ dose of APRL (NS). The fall in both parameters is most likely due to decreased filling of the heart since the venous pressure measured near the right atrium ($2.5\pm0.5$ mmHg) did not change. At the higher doses of APRL, some of the lipid possibly could reach the venous side of the circulation and cause venodilation and pooling of blood.

At the three smallest doses of APRL the blood pressure fell almost entirely as a result of the decrease in peripheral resistance, while the fall in cardiac index contributed a sizeable proportion at 0.5 μg and above. At the highest dose (1 μg) of APRL, the total peripheral resistance fell 41% while the cardiac index fell 28%.

B. Prolonged Depressor Effect

1KGH was produced in three month old rats as related above. Three months later the abdominal aorta below the renal arteries and the inferior vena cava at a parallel level were cannulated as previously described (Muirhead and Brooks, DHEW Publ. No. 8 N1H]78-1473, pp. 5–14). Seven days later the arterial pressure was measured in an automated tail-cuff device, also previously described (Muirhead and Brooks, supra), in order to establish the existence of hypertension.

There were two groups of 10 rats each studied. In group 1, five animals were given APRL intravenously as three separate doses (25 μg of material in 1 ml of saline containing 1 μg/ml of lecithin given in 20 minutes) on two consecutive days at hours designated as 0, 3 and 6 and 24, 27 and 30. Five paired controls received only the vehicle at the same intervals. The pre-injection hypertension MAP was derived by averaging five determinations made on separate days of the week before the experiment plus the pre-injection determination.

The MAP was determined before each injection and at 24, 48, 72, 96 and 120 hours.

In group 2, on eight occasions involving five animals, an eight hour continuous intravenous infusion of 100 μg of APRL was given on two successive days in a total volume of 1 ml of 2% rat albumin in saline. A 30 second sonication procedure was used once more to make certain all of the lipid was dissolved. On seven occasions, four controls were given only the vehicle under identical circumstances. The infusion was conducted through a standardized leak-pump system previously described (Muirhead and Brooks, supra). Before the infusions and on the third day, i.e., ~18 hours after the end of the second infusion, the MAP, CO and hematocrit values were determined.

The CO was determined in unanesthetized animals by the $^{86}$Rb technic (Duling and Weiner, *Proc. Soc. Exp. Biol. Med.* 139:607–709, 1972), which has been validated in our laboratory by comparison with a flowmeter (Muirhead et al., *Circ. Res.* 43 (Supp. 1):53–59, 1978). The technic consists of injecting, as a bolus, 1.0 μCi of $^{86}$Rb in 0.1 ml of saline into the inferior vena cava, while simultaneously withdrawing blood from the aorta at 0.4 ml/min for 25 seconds. The samples were diluted with distilled water to a constant volume to hemolyze the erythrocytes and $^{86}$Rb activity was determined on a Micromedic System model 588 gamma counter. The CO was calculated as follows: CO=($^{86}$Rb injected/$^{86}$Rb withdrawn)×0.4 ml/min. The cardiac index (CI) was calculated by dividing the CO by the weight of the animal in kilograms and the total peripheral vascular resistance (TPVR) was calculated by dividing the MAP by the CI. Immediately after the aortic blood sample was withdrawn, a capillary tube was filled for determination of the microhematocrit value. The MAP was again measured and found to be unchanged.

With respect to group 1, the first two doses of APRL caused a substantial depression of the MAP (~−30 mmHg). Twenty hours after the third dose the MAP remained depressed. The three additional doses of day 2 caused the MAP to be lowered slightly further (to ~−38 mmHg). Of special note was the prolonged depression 20–72 hours after the last dose. The paired controls had no change in MAP.

For this group, eventual recovery of the MAP was not evident until 60–90 hours after the last dose of day 2.

We have reproduced this prolonged depressor effect due to multiple doses of APRL to groups of animals on eight separate occasions.

With respect to group 2, APRL infusions caused a sustained decrease in the blood pressure (34 mmHg) of these hypertensive animals which was due to a significant decrease in total peripheral resistance with no change in the cardiac index. It may be emphasized that the hemodynamic measurements shown here were taken on the day following the termination of the APRL infusion. The hematocrit did not differ from control values, which indicates that the fall in resistance is due to vasodilatation and not to a change in blood viscosity. An unchanged hematocrit is also an indication that blood volume remained the same, even though there was a slight decrease in body weight of both groups. The slight, but statistically insignificant, fall in hematocrit compared to pretreatment levels is probably due to the infusions which contained 2% rat albumin which would be partly retained in the plasma compartment. The non-significant fall in body weight is most likely due to the inability of the animals to eat and drink during the two eight hour periods of infusion.

The data were statistically analyzed by the Student's t or paired t test as appropriate. The null hypothesis was rejected at $p<0.05$.

EXAMPLE 8

The biological activity of APRL was compared to several compounds commonly used for treating hypertension. The initial depression effect of these compounds when injected intravenously into rats (approx. 380 g) was monitored using a Statham P-23 Dc transducer and a Grass continuous recorder. The initial depressor response was quantified in two ways. First, the initial drop in pressure was measured from the recording in millimeters. Second, after the initial drop the pressure started rise to a level where the compound maintained a prolonged effect. This rise in combination with the initial drop forms an apparent right triangle on the recording and the area of this triangle in mm$^2$ was measured. The following results were obtained:

| Compound | Initial Drop, mm/μg | Triangular Area, mm$^2$/μg |
|---|---|---|
| APRL | 3.0 | 4.6 |
| Diazoxide | 0.0068 | 0.0027 |
| Nitroprusside | 0.007 | 0.108 |
| Hydralazine Hydrochloride | — | — |

Hydralazine hydrochloride was also compared to APRL for prolonged antihypertensive effect. A 970 μg dose of hydralazine hydrochloride injected intravenously into a rat (approx. 380 g) caused the blood pressure to drop from 190 mm Hg to 140 mm Hg. Similarly a 100 μg dose of APRL caused the blood pressure of the rat to drop from 185 mm Hg to 150 mm Hg. Thus, hydralazine hydrochloride caused a blood pressure depression of 0.051 mm Hg/μg whereas the APRL of the present invention caused a blood pressure depression of 0.35 mm Hg/μg.

Thus, it can be seen that APRL is about 43 times more effective than nitroprusside in its initial depressor effect and 7 times more effective than hydralizine hydrochloride in its prolonged depressor effect.

The invention has been described in detail with particular reference to the preferred embodiments thereof. However, it will be appreciated that those skilled in the art may make modifications within the spirit and scope of this invention.

We claim:

1. An antihypertensive agent having the formula:

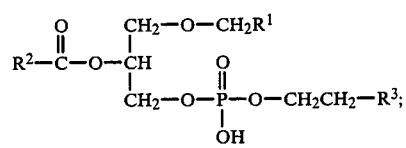

wherein

R$^1$ is an alkyl or alkenyl group having from about 11 to about 23 carbon atoms;

R$^2$ is hydrogen or an alkyl or alkenyl group having from about 1 to about 11 carbon atoms; and R$^3$ is NR$_4$R$_5$ or NR$_4$R$_5$R$_6$$^+$An$^-$ wherein $R_4$, $R_5$ and $R_6$ are independently hydrogen or lower alkyl having from 1 to 3 carbon atoms and An is an anion;

said agent having a biological depressor effect activity of at least 0.2 units.

2. The antihypertensive agent of claim 1 wherein $R^1$ has from about 13 to about 19 carbon atoms.

3. The antihypertensive agent of claim 1 wherein $R^2$ has from 1 to about 4 carbon atoms.

4. The antihypertensive agent of claim 1 wherein $R^1$ has from about 15 to 17 carbon atoms and $R^2$ is methyl.

5. The antihypertensive agent of claim 1 having a biological activity of at least 10 units.

6. The antihypertensive agent of claim 1, said agent being selected from the group consisting of phosphoric acid (2-acetoxy-3-hexadecyloxy propyl)-2-aminoethyl ester phosphoric acid (2-acetoxy-3-hexadecyloxy propyl)[(N-2-ethyl)trimethylammonium hydroxide]ester phosphoric acid [2-acetoxy-(3-hexadec-en-oxy)propyl]-2aminoethyl ester phosphoric acid [2-acetoxy-(3-hexadec-en-oxy)propyl]-[(N-2-ethyl)trimethylammonium hydroxide]ester phosphoric acid (2-acetoxy-3-heptadecyloxy propyl)-2-aminoethyl ester phosphoric acid (2-acetoxy-3-heptadecyloxy propyl)-[N-2-ethyl)trimethylammonium hydroxide]ester phosphoric acid [2-acetoxy-(3-heptadec-en-oxy)-propyl]-2-aminoethyl ester phosphoric acid [2-acetoxy-(3-heptadec-en-oxy)-propyl]-[(N-2-ethyl)trimethylammonium hydroxide]ester phosphoric acid (2-acetoxy-3-octadecyloxy propyl)-2-aminoethyl ester phosphoric acid(2-acetoxy-3-octadecyloxy propyl)-[(N-2-ethyl)trimethylammonium hydroxide]ester phosphoric acid [2-acetoxy-(3-octadec-en-oxy)propyl]-2-aminoethyl]ester phosphoric acid [2-acetoxy-(3-octadec en-oxy)propyl]-[(N-2-ethyl)trimethylammonium hydroxide]ester.

7. The antihypertensive agent of claim 1 wherein $R^2$ is methyl.

8. The antihypertensive agent of claim 1 having a biological activity of at least 40 units.

9. A compound of the formula $$\begin{array}{c} \text{O} \quad\quad \text{CH}_2-\text{O}-\text{CH}_2\text{R}^1 \\ \| \quad\quad\quad | \\ \text{R}_2-\text{C}-\text{O}-\text{CH} \quad\quad \text{O} \\ | \quad\quad\quad \| \\ \text{CH}_2\text{O}-\text{P}-\text{OCH}_2\text{CH}_2-\text{R}^3 \\ | \\ \text{OH} \end{array}$$

wherein $R^1$ is an alkyl group having from about 11 to 23 carbon atoms;

$R^2$ is hydrogen or an alkyl group having from about 1 to about 11 carbon atoms; and $R^3$ is $NR_4R_5$ or $N^+R_4R_5R_6An^-$ wherein $R_4$, $R_5$ and $R_6$ are independently hydrogen or lower alkyl having from 1 to 3 carbon atoms and An is an anion; said compound having a biological depressor effect activity of at least 0.2 units.

10. A compound of claim 9 wherein $R_2$ is methyl and $R_3$ is $N^+(CH_3)_3$.

11. A compound selected from the group consisting of (1) phosphoric acid (2-acetoxy-3-hexadecyloxy propyl) [(N-2-ethyl)trimethylammonium hydroxide]ester; (2) phosphoric acid (2-acetoxy-3-hexadec-en-oxy propyl) [(N-2-ethyl)trimethylammonium hydroxide]ester; and (3) phosphoric acid (2-acetoxy-3-octadec-en-oxy propyl) [(N-2-ethyl)trimethylammonium hydroxide]ester.

12. Phosphoric acid (2-acetoxy-3-hexadecyloxy propyl) [(N-2-ethyl)trimethylammonium hydroxide]ester.

13. A platelet activating factor consisting essentially of the compound recited in claim 11.

14. A platelet activating factor consisting essentially of the compound recited in claim 12.

15. A pharmaceutical preparation for treating hypertensive mammals, said preparation comprising a pharmaceutically acceptable carrier and an effective antihypertensive treatment amount of a compound having the formula:

$$\begin{array}{c} \text{O} \quad\quad \text{CH}_2-\text{O}-\text{CH}_2\text{R}^1 \\ \| \quad\quad\quad | \\ \text{R}^2-\text{C}-\text{O}-\text{CH} \quad\quad \text{O} \\ | \quad\quad\quad \| \\ \text{CH}_2-\text{O}-\text{P}-\text{O}-\text{CH}_2-\text{CH}_2-\text{R}^3 \\ | \\ \text{OH} \end{array}$$

wherein:

$R^1$ is an alkyl or alkenyl group having from about 11 to about 23 carbon atoms;

$R^2$ is hydrogen or an alkyl or alkenyl group having from about 1 to about 11 carbon atoms; and $R^3$ is $NR_4R_5$ or $NR_4R_5R_6^+An^-$ wherein $R_4$, $R_5$ and $R_6$ are independently hydrogen or lower alkyl having from about 1 to 3 carbon atoms and An is an anion;

or a pharmaceutically acceptable salt thereof.

16. The pharmaceutical preparation of claim 15 wherein said carrier comprises saline.

17. The pharmaceutical preparation of claim 15 in tablet form.

18. The pharmaceutical preparation of claim 15 in a unit dose form.

19. The pharmaceutical preparation of claim 18 in which said dose is in the range of from about 2 mg to about 5 mg.

20. A composition comprising the compound recited in claim 9 in combination with a pharmaceutically acceptable diluent.

21. A composition comprising the compound recited in claim 10 in combination with a pharmaceceutically acceptable diluent.

22. A composition comprising the compound recited in claim 11 in combination with a pharmaceutically acceptable diluent.

23. A composition comprising the compound recited in claim 12 with a pharmaceutically acceptable diluent.

* * * * *